(12) United States Patent
Øhlenschlæger

(10) Patent No.: US 7,335,224 B2
(45) Date of Patent: Feb. 26, 2008

(54) STENT GRAFT RETENTION SYSTEM

(75) Inventor: Bent Øhlenschlæger, Lille Skensved (DK)

(73) Assignees: William Cook Europe ApS, Bjaerskov (DK); Cook Incorporated, Bloomington, IN (US)

( * ) Notice: Subject to any disclaimer, the term of this patent is extended or adjusted under 35 U.S.C. 154(b) by 300 days.

(21) Appl. No.: 10/962,764

(22) Filed: Oct. 12, 2004

(65) Prior Publication Data
US 2005/0107862 A1    May 19, 2005

Related U.S. Application Data

(60) Provisional application No. 60/510,228, filed on Oct. 10, 2003.

(51) Int. Cl.
*A61F 2/06* (2006.01)
(52) U.S. Cl. .................. 623/1.11; 623/1.12; 623/1.23
(58) Field of Classification Search ............... 623/1.12, 623/1.11, 1.23; 606/108
See application file for complete search history.

(56) References Cited

U.S. PATENT DOCUMENTS 5,776,142 A * 7/1998 Gunderson .................. 623/1.11
2001/0037142 A1 * 11/2001 Stelter et al. .............. 623/1.13

* cited by examiner

*Primary Examiner*—Anhtuan T. Nguyen
*Assistant Examiner*—Timothy J Neal
(74) *Attorney, Agent, or Firm*—Richard J. Godlewski

(57) ABSTRACT

A retention system for retaining a stent graft (13) onto a deployment device (1) in which the stent graft has an exposed stent (11) at at least one end. The deployment device has a capsule (7) to receive the exposed stent during deployment and an arrangement to move the capsule to release the exposed stent when required. A release wire (17) associated with the deployment device engages a portion (19) of the exposed stent within the capsule to retain the exposed stent in the capsule. At least one retention loop (25) on the stent graft is connected around the release wire to prevent removal of the capsule from the exposed stent until the release wire has been removed from its engagement with the exposed stent within the capsule and the retention loop is released.

12 Claims, 4 Drawing Sheets

STENT GRAFT RETENTION SYSTEM

CROSS-REFERENCE TO RELATED APPLICATIONS

This application claims priority of provisional application Ser. No. 60/510,228, filed Oct. 10, 2003.

TECHNICAL FIELD

This invention relates to a medical device and more particularly a medical device for the deployment of a stent graft into the human or animal body.

BACKGROUND OF THE INVENTION

A stent graft can be deployed into the vasculature of a patient to repair a defect in the vasculature such as an aortic dissection or an abdominal or thoracic aortic aneurism.

Some stent grafts for the treatment of aortic dissections or an abdominal or thoracic aortic aneurysms include an exposed stent extending distally or proximally from the stent graft. Such a stent graft can include one of more barbs to assist with retention of the exposed stent into the vasculature of a patient and hence to prevent inadvertent or early engagement of the barbs with the vasculature when deploying the stent graft and introduction device for the stent graft may include a capsule which encompasses the exposed stent and the barbs. To release the exposed stent the capsule is moved relative to the stent graft and exposed stent.

It is desirable, however, that premature release does not occur and hence it has been proposed to use a release wire which passes through an aperture in the capsule and engages part of the exposed stent within the capsule.

This arrangement does not prevent relative rotation of the stent graft with respect to the introduction device and capsule nor can it entirely prevent premature release. Rotation of the exposed stent within the capsule can also cause entanglement of the struts of the exposed stent which can cause problems on deployment.

The object of this invention is to provide a safety release mechanism such as a stent graft retention system to at least prevent premature release of the stent graft and particularly the exposed stent from the capsule. It is a further object to prevent undesirable rotation of the stent graft with respect to its retention mechanism.

Throughout this specification the term distal with respect to a portion of the aorta, a deployment device or a stent graft or prosthesis is the end of the aorta, deployment device or stent graft further away in the direction of blood flow away from the heart and the term proximal means the portion of the aorta, deployment device or end of the stent graft nearer to the heart. When applied to other vessels similar terms such as caudal and cranial should be understood.

SUMMARY OF THE INVENTION

In one form therefore although this may not necessarily be the only or broadest form, the invention is said to reside in a retention system for retaining a stent graft onto a deployment device, the stent graft being of a type having an exposed stent at at least one end thereof and the deployment device including a capsule to receive the exposed stent during deployment and an arrangement to move the capsule with respect to the exposed stent to release the exposed stent when required. The retention system further includes a release wire associated with the deployment device to engage a portion of the exposed stent within the capsule and hence retain the exposed stent in the capsule and at least one retention loop on the stent graft, the release wire passing through the retention loop to prevent removal of the capsule from the exposed stent until the release wire has been removed from its engagement with the exposed stent within the capsule and with the at least one retention loop.

Preferably the release wire passes through an aperture in the capsule and the at least one retention loop is engaged to the release wire where it passes through the aperture in the capsule.

There may be provided two retention loops which are positioned on diametrically opposed sides of the stent graft whereby to also prevent relative rotation between the stent graft and deployment device as well as to prevent premature release.

In one embodiment the exposed stent on the stent graft may be a distally extending exposed stent. In an alternative embodiment the exposed stent may be a proximally extending exposed stent.

The at least one retention loop preferably remains with the stent graft after deployment.

It will be noted that by this arrangement the retention loop acts to prevent the stent graft from being prematurely pulled out of the capsule.

In the case of a stent graft suitable for treatment of a thoracic aortic aneurism the exposed stent may be a distally extending exposed stent and in the case of a stent graft suitable for treatment of an abdominal aortic aneurism the exposed stent may be a proximally extending exposed stent.

In a further form the invention maybe said to reside in a stent graft deployment device including a stent graft retained thereon, the stent graft deployment device comprising a deployment catheter, a proximally opening capsule at the proximal end of the deployment catheter with an exposed stent of the stent graft being received in the capsule, and a trigger wire release mechanism including a trigger wire engaging the exposed stent of the stent graft in the capsule, a retention arrangement extending from the stent graft to engage the trigger wire at the capsule, wherein the exposed stent of the stent graft cannot be removed from the capsule until the trigger wire has been removed and the retention arrangement released.

In one embodiment the retention arrangement extending from the stent graft to the trigger wire at the capsule comprises at least one loop of a suture material. Alternatively it comprises two loops of a suture material with the loops engaging the stent graft at diametrically opposed sides of the stent graft.

In a further form the invention comprises a stent graft deployment device including a stent graft retained thereon, the stent graft deployment device comprising a deployment catheter extending to a nose cone dilator at its proximal end, a distally opening capsule at the distal end of the nose cone dilator with a proximally extending exposed stent of the stent graft being received in the capsule, and a trigger wire release mechanism including a trigger wire engaging the exposed stent of the stent graft in the capsule, a retention arrangement extending from the stent graft to engage the trigger wire at the capsule, wherein the exposed stent of the stent graft cannot be removed from the capsule until the trigger wire has been removed and the retention arrangement released.

In one embodiment the retention arrangement extending from the stent graft to the trigger wire at the capsule comprises at least one loop of a suture material. Alternatively it comprises two loops of a suture material with the loops engaging the stent graft at diametrically opposed sides of the stent graft.

The graft material from which the covering of the stent graft of the present invention may be formed may be a synthetic material such as DACRON, expanded polytetrafluoroethylene (ePTFE), or other synthetic biocompatible materials. Alternatively a naturally occurring biomaterial, such as collagen, is highly desirable, particularly a specially derived collagen material known as a collagenous extracellular matrix (ECM) material, such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in venous valves can be replaced by native tissue in as little as a month's time. In addition to xenogenic biomaterials, such as SIS, autologous tissue can be harvested as well. Additionally Elastin or Elastin-Like Polypetides (ELPs) and the like offer potential as a material to fabricate the covering or frame to form a device with exceptional biocompatibility. Another alternative would be to use allographs such as harvested native valve tissue. Such tissue is commercially available in a cryopreserved state.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting, replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO99/29262 entitled "Endoluminal Aortic Stents" discloses a fenestrated prosthesis for placement where there are intersecting arteries. This feature and other features disclosed in PCT Patent Publication No. WO99/29262 could be used with the present invention and the disclosure of PCT Patent Publication No. WO99/29262 is herewith incorporated in its entirety into this specification.

PCT Patent Publication No. WO03/034948 entitled "Prostheses for Curved Lumens" discloses prostheses with arrangements for bending the prosthesis for placement into curved lumens. This feature and other features disclosed in PCT Patent Publication No. WO03/034948 could be used with the present invention and the disclosure of PCT Patent Publication No. WO03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, and Published on Dec. 18, 2003, as U.S. Patent Application Publication No. US-2003-0233140-A1 entitled "Trigger Wires" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1 could be used with the present invention and the disclosure of U.S. Provisional Patent Application Ser. No. 60/392,682, U.S. patent application Ser. No. 10/447,406, and U.S. Patent Application Publication No. US-2003-0233140-A1 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as U.S. Patent Application Publication No. US-2004-0098079-A1 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and U.S. Patent Application Publication No. US-2004-0098079-A1 could be used with the present invention and the disclosure of U.S. Provisional Patent Application Ser. No. 60/392,667, U.S. patent application Ser. No. 10/609,846, and U.S. Patent Application Publication No. US-2004-0098079-A1 are herewith incorporated in their entirety into this specification U.S. Provisional Patent Application Ser. No. 60/391,737, filed Jun. 26, 2002, U.S. patent application Ser. No. 10/602,930, filed Jun. 24, 2003, and published on Mar. 18, 2004, as U.S. Patent Application Publication No. US-2004-0054396-A1 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602, 930, and U.S. Patent Application Publication No. US-2004-0054396-A1 could be used with the present invention and the disclosure of U.S. Provisional Patent Application Ser. No. 60/391,73, U.S. patent application Ser. No. 10/602,930, and U.S. Patent Application Publication No. US-2004-0054396-A1 are herewith incorporated in their entirety into this specification.

U.S. Provisional Patent Application Ser. No. 60/405,367, filed Aug. 23, 2002, U.S. patent application Ser. No. 10/647, 642, filed Aug. 25, 2003, and published on Apr. 15, 2004, as U.S. Patent Application Publication No. US-2004-0073289-A1 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1 could be used with the present invention and the disclosure of U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1 are herewith incorporated in their entirety into this specification.

PCT Patent Publication No. WO03/053287 entitled "Improving Graft Adhesion" discloses arrangements on stent grafts for enhancing the adhesion of such stent grafts into walls of vessels in which they are deployed. This feature and other features disclosed in PCT Patent Publication No. WO03/053287 could be used with the present invention and the disclosure of PCT Patent Publication No. WO03/053287 is herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and published on Apr. 29, 2004, as U.S. Patent Application Publication No. US-2004-0082990-A1 entitled "Composite Prostheses" discloses prostheses or stent grafts suitable for endoluminal deployment. These prostheses and other features disclosed in U.S. Provisional Patent Application Ser. No. 60/405,769, U.S. patent application Ser. No. 10/645,095, and U.S. Patent Application Publication No. US-2004-0082990-A1, could be used with the present invention and the disclosure of U.S. Provisional Patent Application Ser. No. 60/405,769, U.S. patent application Ser. No. 10/645,095, and U.S. Patent Application Publication No. US-2004-0082990-A1 are herewith incorporated in its entirety into this specification.

BRIEF DESCRIPTION OF THE DRAWING

This then generally describes the invention but to assist with understanding, reference will now be made to the accompanying drawings which show a preferred embodiment of the invention.

In the drawings.

DETAILED DESCRIPTION

Figure 1:
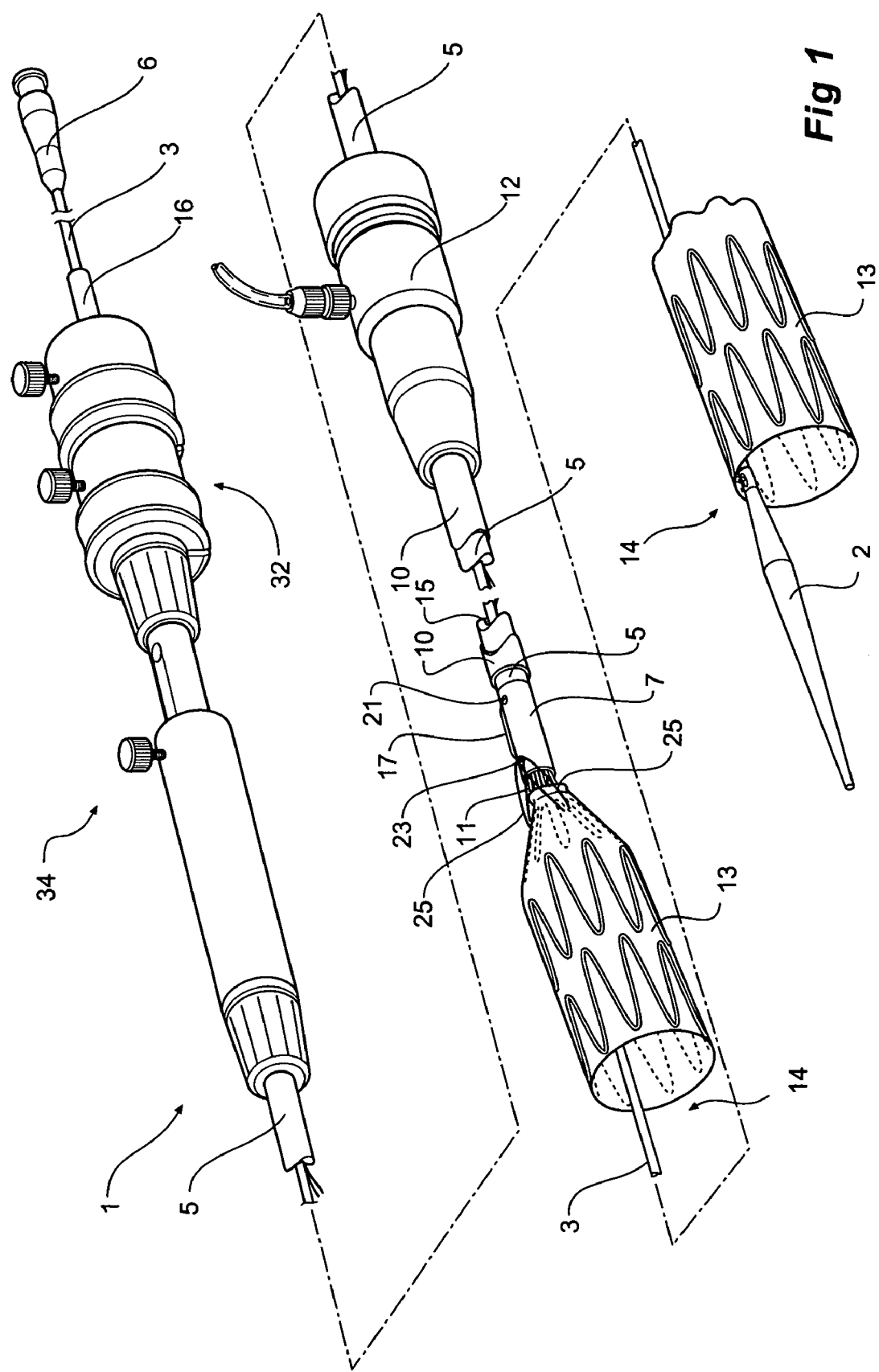
FIG. 1 shows a stent graft deployment device incorporating one embodiment of the present invention.

Now looking more closely to the drawings and particularly FIG. 1 it will be seen that a deployment device generally shown as 1 includes a guide wire catheter 3 which extends through the deployment device 1. At the proximal end of the guide wire catheter 3 is a nose cone dilator 2 and at the distal end is a male Luer lock connector 6 through which radiographic fluids and the like may be administered. A capsule catheter 5 which includes a capsule 7 at its proximal end has a longitudinally extending lumen 15 and the capsule catheter 5 is coaxially mounted onto the guide wire catheter 3 with the guide wire catheter 3 extending through the lumen 15. The capsule catheter 5 extends from a distal handle 34 which in use remains outside a patient to the capsule 7 at its proximal end. The handle 34 includes a trigger wire release mechanism generally shown as 32.

Between the nose cone dilator 2 and the capsule 7 there is a region 8 into which a stent graft 13 is retained for deployment. The capsule 7 has a proximally facing internal recess 9 (See FIG. 3) into which is received a distally extending exposed stent 11 of the stent graft 13. The capsule catheter 5 can move longitudinally with respect to the guide wire catheter 3 upon release of a pin vice 16. A sheath 10 extends from a sheath manipulator 12 over the capsule catheter 5 and in the ready to deploy position extends to the nose cone dilator 2 and retains the stent graft 13 in a compressed state. As shown in FIG. 1, however, the sheath 10 has been withdrawn to distal of the capsule 7 to partially release the stent graft 13. The stent graft 13 is, however, still retained by the distally extending exposed stent 11 of the stent graft 13 being retained with in the capsule 7 and a proximal retention generally shown as 14.

Figure 2:
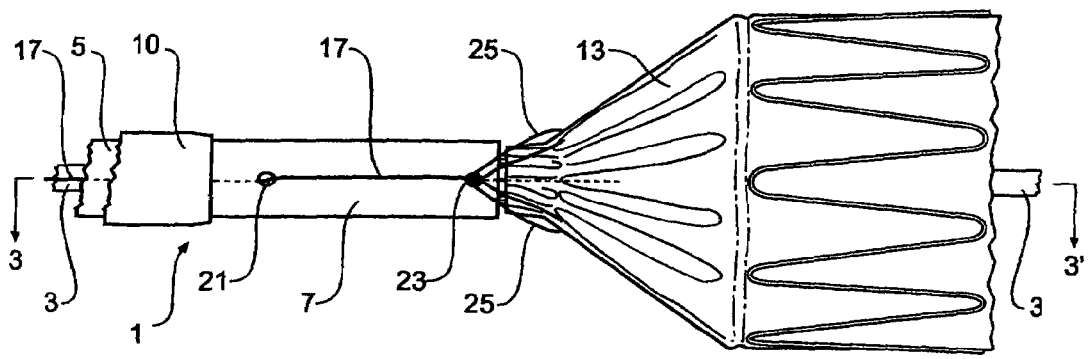
FIG. 2 shows a portion of a deployment device and stent graft at one stage during the deployment process.
Figure 3:
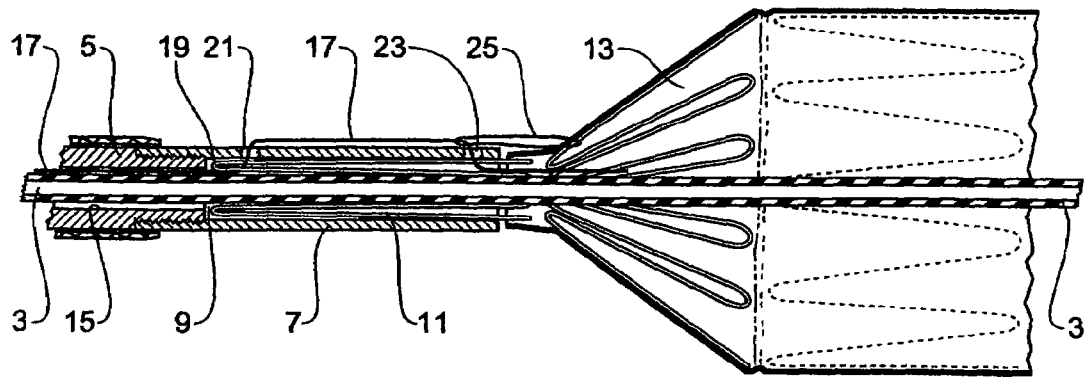
FIG. 3 shows a cross-sectional view of the embodiment shown in FIG. 1.
Figure 4:
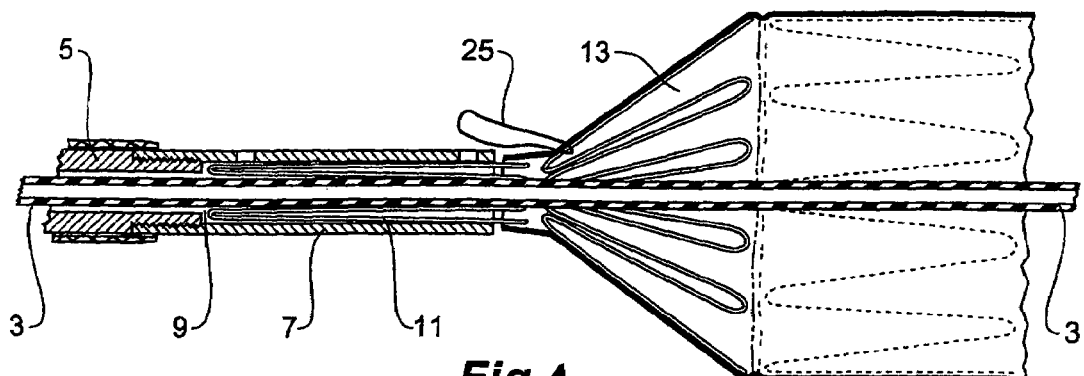
FIG. 4 shows the arrangement of FIG. 2 but with the release wire withdrawn.
Figure 5:
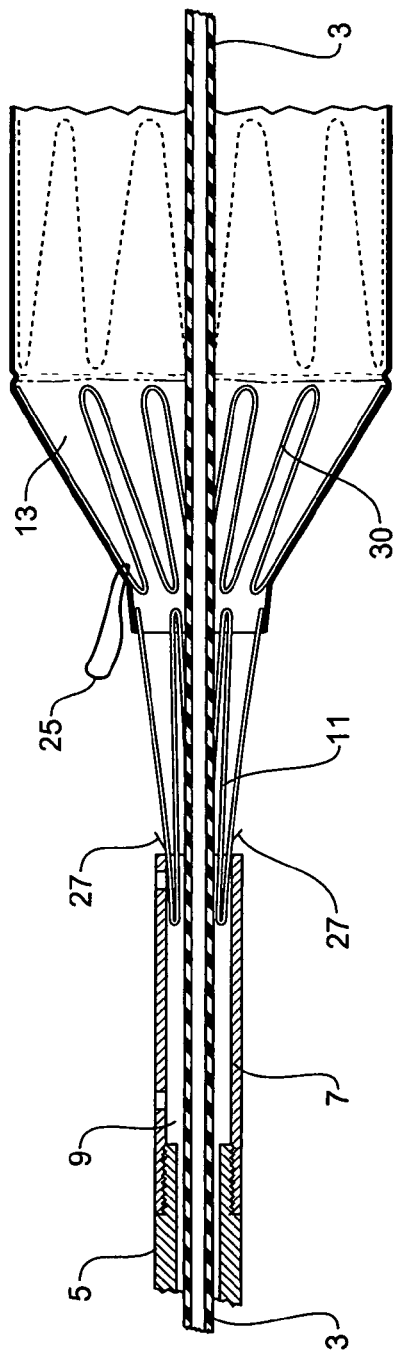
FIG. 5 shows the embodiment of FIG. 3 with the capsule partially retracted.

FIGS. 2 to 5 show detail of the capsule region of the deployment device with FIGS. 3 to 5 being cross sectional views along the line 3-3' in FIG. 2.

As depicted in FIGS. 2 and 3 the stage of deployment of the stent graft is that at which the sheath 10 which is used to cover the stent graft 13 during introduction, has been retracted to release the stent graft 13 from a restricted condition except where it is still retained by the capsule 7. The stent graft 13 is retained by the distally extending exposed stent 11 of the stent graft 13 being retained within the capsule 7.

Passing through the lumen 15 of the catheter 5 is a release wire 17 which passes into the internal recess 9 and within the internal recess 9 in the capsule 7 the release wire 17 passes through a loop 19 of the exposed stent 11 and then through an aperture 21 in the capsule 7. The release wire 17 then passes through another aperture 23 back into the capsule internal recess 9 and terminates within the stent graft 13. At least one retention loop 25 of suture material or similar material is engaged into the material of the stent graft 13 and at its other end is looped around the release wire 17 where it passes into the aperture 23 in the capsule 7.

In FIG. 2 two retention loops 25 can be seen and these are placed substantially diametrically opposite to each other where the engage into the material on the distal end of the stent graft 13. By spacing the two retention loops 25 substantially diametrically opposite to each other on the stent graft 13 undesirable rotation of the stent graft 13 with respect to the capsule catheter may be prevented. In practice the stent graft 13 would be mounted onto the deployment device and the release wire 17 put in place and then a length of suture material would be stitched into the graft material of the stent graft and passed around the release wire 17 and then knotted to form the loop 25.

As can be seen in FIG. 4 the release wire has been removed from the introducer device by actuation of the trigger wire release mechanism 32 on the handle 34 (see FIG. 1) and hence the loop 25 is no longer retained by the release wire and the loop 19 of the exposed stent 11 is also not retained.

At this stage, therefore, the capsule catheter 5 can be moved distally with respect to the guide wire catheter 3 so that the situation in FIG. 5 occurs. At this stage the exposed stent 11 exits the internal recess 9 and is partially freed from its engagement within the capsule 7 and the distal end of the stent graft 13 has started to expand under the action of the distal-most self expanding zig zag stent 30. The barbs 27 on the exposed stent 11 are now exposed.

Figure 6:
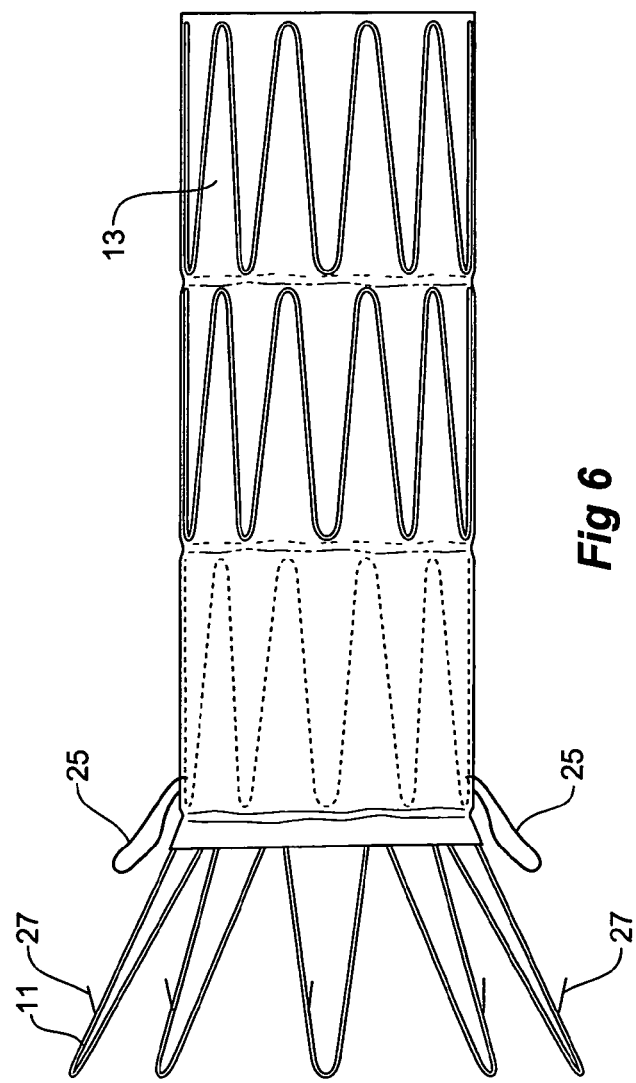
FIG. 6 shows a portion of the deployed stent graft and particularly showing the retention loops still on the stent graft.

FIG. 6 shows a portion of the fully expanded stent graft 13. The exposed stent 11 has expanded such that the barbs 27 which were within the capsule 7 and hence not able to prematurely engage the vasculature of a patient have now been released and can engage the vasculature to hold the stent graft in the selected place. It will be noted, too, that the retention loops 25 are still engaged with the stent graft 13 and these remain with the stent graft. Being on the outside of the stent graft, however, they do not interfere with flow of blood through the stent graft.

Generally it will be seen that by this arrangement the exposed stent on the stent graft is prevented from either moving longitudinally or rotating with respect to the capsule in which it is retained by use of the safety retention loops of the present invention.

This embodiment of the invention has been depicted in respect to a distally extending exposed stent on the stent graft and a capsule catheter with a proximal facing opening to the capsule on the capsule catheter. It will be realised, however, that in another embodiment the capsule may be distally opening and associated with the nose cone dilator and a proximally extending exposed stent on the stent graft. Such an arrangement is shown in FIG. 7.

Figure 7:
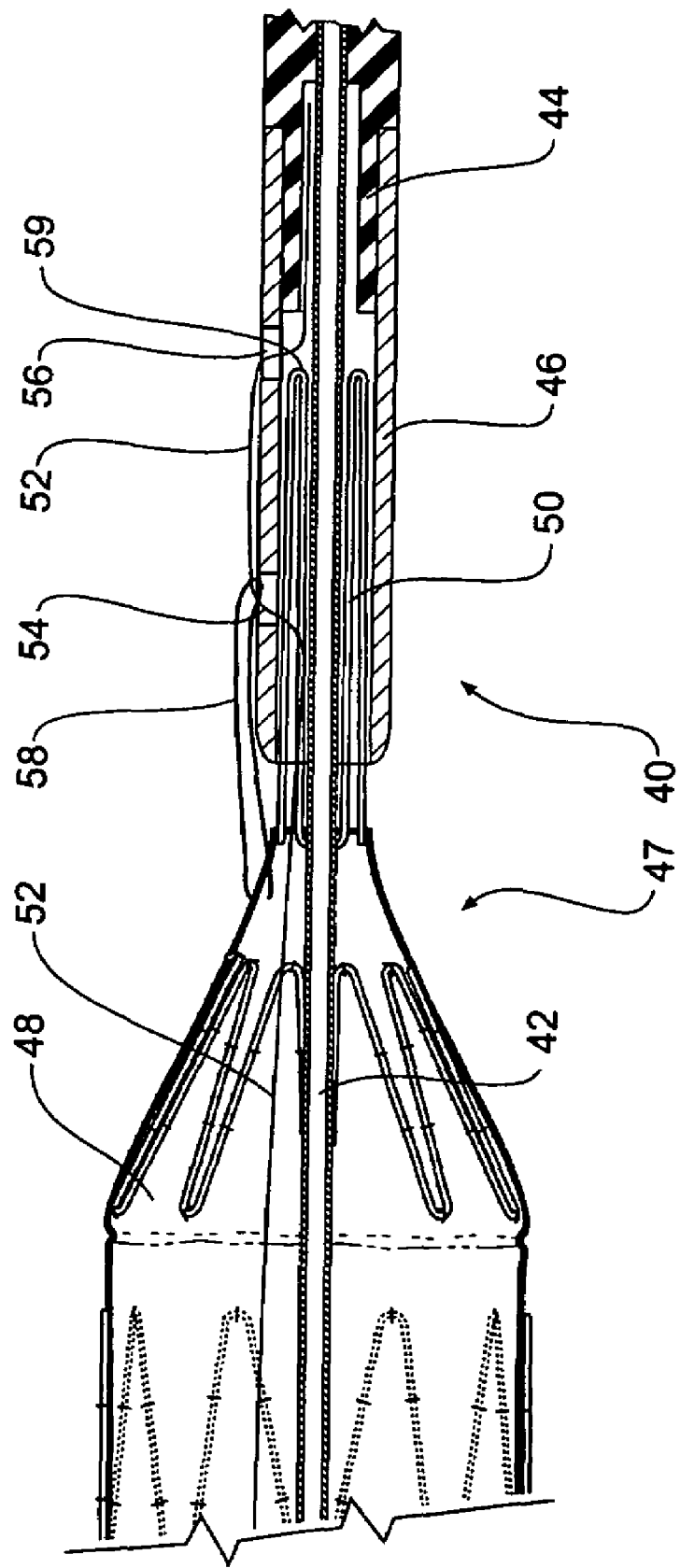
FIG. 7 shows an alternative embodiment of the invention suitable for a proximally extending exposed stent on a stent graft.

FIG. 7 shows cross sectional detail of a proximal region of a deployment device. The deployment device 40 has a guide wire catheter 42 with a nose cone dilator 44 at its proximal end. At the distal end of the nose cone dilator 44 is a distally opening capsule 46. The proximal end 47 stent graft 48 is restrained by its proximally extending exposed stent 50 being received in the capsule 46. A trigger release wire 52 extends from a release mechanism (not shown) through the stent graft 48 and out of the capsule through an aperture 54 in the capsule and back in again through another aperture 56 where it passes through one of the loops 59 of the proximally extending exposed stent 50 before terminating within the nose cone dilator 44. A retention loop 58 is engaged with the material of the stent graft 48 and around the trigger release wire 52 where it exits from the capsule 46 at aperture 54. The retention loop 58 is preferably formed from a length of suture material. This retention loop 58 prevents the stent graft 48 from either moving longitudinally or undesirably rotating with respect to the capsule 46 until the trigger release wire 52 is removed.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A retention system for retaining a stent graft onto a deployment device in combination with a stent graft retained on the deployment device, the stent graft having an exposed stent at at least one end thereof and the deployment device including a capsule to receive the exposed stent during deployment and an arrangement to move the capsule with respect to the exposed stent to release the exposed stent, the capsule comprising an aperture therein, the retention system comprising a release wire associated with the deployment device to engage a portion of the exposed stent wthin the capsule and to retain the exposed stent in the capsule and at least one retention loop on the stent graft, the retention loop comprising a length of suture material stitched into the stent graft and passed around the release wire, the release wire passing through the retention loop to prevent removal of the capsule from the exposed stent until the release wire has been removed from its engagement with the exposed stent within the capsule and with the at least one retention loop and wherein the release wire passes through the aperture in the capsule and the at least one retention loop is engaged around the release wire where it exits the aperture in the capsule.

2. A retention system as in claim 1 wherein there are two retention icops which are positioned on diametrically opposed sides of the stent graft whereby to also prevent relative rotation between the stent graft and deployment device as well as to prevent premature release.

3. A retention system as in claim 1 wherein the exposed stent is a distally extending exposed stent.

4. A retention system as in claim 1 wherein the exposed stent is a proximally extending exposed stent.

5. A retention system as in claim 1 wherein the at least one retention loop remains with the stent graft after deployment.

6. A retention system as in claim 1 wherein graft material from which a covering of the stent graft of the present invention is formed is selected from the group comprising a biocompatible synthetic material, expanded polytetrafluoro-ethylene (ePTFE), a naturally occurring biomaterial or colleganous extracellular matrix (ECM) material.

7. A stent graft deployment device including a stent graft retained thereon, the stern graft deployment device comprising a deployment catheter, a proximally opening capsule at the proximal end of the deployment catheter with an exposed stent of the stent graft being received in the capsule, and a trigger wire release mechanism including a trigger wire engaging the exposed stent of the stern graft in the capsule, a retention arrangement extending from the stent graft to engage the trigger wire at the capsule, wherein the exposed stent of the stent graft cannot be removed from the capsule until the trigger wire has been removed and the retention arrangement released, the retention arrangement comprising a retention loop, the retention loop comorising a length of suture material stitched into the stent graft and passed around the trgger wire.

8. A stent graft deployment device as in claim 7 wherein the retention arrangement extending from the stent graft to the trigger wire at the capsule comprises at least one loop of a suture material.

9. A stent graft deployment device as in claim 7 wherein the retention arrangement extending from the stent graft to the trigger wire at the capsule comprises two loops of a suture material with the loops engaging the stent graft at diametrically opposed sides of the stent graft.

10. A stent graft deployment device including a stent graft retained thereon, the stent graft deployment device comprising a deployment catheter extending to a nose cone dilator at its proximal end, a distally opening capsule at the distal end of the nose cone dilator with a proximally extending exposed stent of the stent graft being received in the capsule, and a trigger wire release mechanism including a trigger wire engaging the exposed stent of the stent graft in the capsule, a retention arrangement extending from the stent graft to engage the trigger wire at the capsule, wherein the exposed stent of the stent graft cannot be removed from the capsule until the trigger wire has been removed and the retention arrangement released, the retention arrangement comprising a retention loop, the retention loop comprising a length of suture material stitched into the stent graft and passed around the trigger wire.

11. A stent graft deployment device as in claim 10 wherein the retention arrangement extending from the stent graft to the trigger wire at the capsule comprises at least one loop of a suture material.

12. A stent graft deployment device as in claim 10 wherein the retention arrangement extending from the stent graft to the trigger wire at the capsule comprises two loops of a suture material with the loops engaging the stent graft at diametrically opposed sides of the stent graft.

* * * * *